(12) United States Patent
Chappel et al.

(10) Patent No.: US 10,286,144 B2
(45) Date of Patent: May 14, 2019

(54) METHOD AND SYSTEM FOR DETECTING MALFUNCTION OF A MEMS MICROPUMP

(75) Inventors: Eric Chappel, Versonnex (FR); Stephan Proennecke, Lausanne (CH); Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 1542 days.

(21) Appl. No.: 14/128,925

(22) PCT Filed: Jun. 22, 2012

(86) PCT No.: PCT/IB2012/053176
§ 371 (c)(1),
(2), (4) Date: Feb. 14, 2014

(87) PCT Pub. No.: WO2012/176170
PCT Pub. Date: Dec. 27, 2012

(65) Prior Publication Data
US 2014/0147246 A1 May 29, 2014

(30) Foreign Application Priority Data

Jun. 23, 2011 (EP) .................................. 11171155
Jul. 4, 2011 (EP) .................................. 11172494

(51) Int. Cl.
| | |
|---|---|
| *A61M 5/14* | (2006.01) |
| *A61M 5/142* | (2006.01) |
| *A61M 5/145* | (2006.01) |
| *A61M 5/168* | (2006.01) |
| *A61M 5/50* | (2006.01) |
| *F04D 15/00* | (2006.01) |

(52) U.S. Cl.
CPC .... *A61M 5/14244* (2013.01); *A61M 5/14593* (2013.01); *A61M 5/16859* (2013.01); *A61M 5/16881* (2013.01); *A61M 5/5086* (2013.01); *F04D 15/0005* (2013.01)

(58) Field of Classification Search
CPC .......... A61M 5/14236; A61M 5/14593; A61M 5/16859; A61M 5/16881; A61M 5/5086; F04D 15/0005
USPC .......................................... 417/413.2, 413.3
See application file for complete search history.

(56) References Cited

U.S. PATENT DOCUMENTS

| | | | | |
|---|---|---|---|---|
| 6,109,889 A | * | 8/2000 | Zengerle | F04B 43/046 417/413.2 |
| 6,869,275 B2 | * | 3/2005 | Dante | F04B 43/046 251/129.06 |

(Continued)

OTHER PUBLICATIONS

International Preliminary Report on Patentability (IPRP Chapter I) and Written Opinion for PCT/IB2012/053176, dated Dec. 23, 2013.

(Continued)

*Primary Examiner* — Timothy L Maust
(74) *Attorney, Agent, or Firm* — Nixon & Vanderhye, P.C.

(57) ABSTRACT

Method for detecting failure including possible under or over delivery of a micropump having at least an inlet valve, a pumping chamber with an inner pressure sensor and an outlet valve, said method comprising the determination of the pump tightness via the measurement of the pressure by said inner pressure sensor in said pumping chamber at least at certain intervals when the pump is inactive and the comparison with a value of reference.

11 Claims, 5 Drawing Sheets

(56) References Cited

U.S. PATENT DOCUMENTS

| | | | | |
|---|---|---|---|---|
| 7,484,940 | B2* | 2/2009 | O'Neill | F04B 43/043 |
| | | | | 417/410.1 |
| 8,920,376 | B2* | 12/2014 | Caffey | A61M 5/14526 |
| | | | | 204/630 |
| 8,979,825 | B2* | 3/2015 | Gray | A61M 5/14593 |
| | | | | 604/891.1 |
| 9,162,024 | B2* | 10/2015 | Pang | A61F 9/00781 |
| 9,199,035 | B2* | 12/2015 | Shih | A61F 9/0017 |
| 9,333,297 | B2* | 5/2016 | Li | G06F 19/3468 |
| 9,555,174 | B2* | 1/2017 | Franano | A61M 1/101 |
| 9,849,238 | B2* | 12/2017 | Li | A61M 5/172 |
| 2007/0270782 | A1* | 11/2007 | Miesel | A61M 5/14276 |
| | | | | 604/891.1 |
| 2011/0142688 | A1 | 6/2011 | Chappel et al. | |
| 2016/0303318 | A1* | 10/2016 | Burke | A61M 5/14276 |

OTHER PUBLICATIONS

International Search Report for PCT/IB2012/053176, dated Oct. 29, 2012.
Written Opinion of the International Searching Authority for PCT/IB2012/053176, dated Oct. 29, 2012.
Stranden, E. et al., "Pressure-vol. recordings of human subcutaneous tissue: A study in patients with edema following arterial reconstruction for lower limb atherosclerosis", Microvascular Research, vol. 24, No. 3, (Nov. 1, 1982), pp. 241-248.

* cited by examiner

Fig. 8

METHOD AND SYSTEM FOR DETECTING MALFUNCTION OF A MEMS MICROPUMP

This application is the U.S. national phase of International Application No. PCT/IB2012/053176, filed 22 Jun. 2012, which designated the U.S. and claims priority to EP Application No. 11171155.2, filed 23 Jun. 2011, and EP Application No. 11172494.4, filed 4 Jul. 2011, the entire contents of each of which are hereby incorporated by reference.

1. FIELD OF INVENTION

The present invention relates to MEMS (Micro-Electro-Mechanical System) micropumps which may be advantageously used for administrating insulin. Such pumps comprise a pumping chamber having a pumping membrane and an integrated sensor comprised between two check valves. More specifically, the present invention concerns the methods for monitoring the state of a MEMS micropump.

2. STATE OF THE ART

The detection of dysfunctions, especially in medical devices, is important because the life of the patient may depend on proper functioning of said devices. In case of infusion pumps, for example, the potentially dangerous results of a failure are typically over-infusion or under-infusion of the drug into the patient.

Examples of dysfunctions are leaks, occlusions or presence of air bubbles in the pumping line.

State-of-the-art devices and methods for detecting dysfunctions in medical devices are for instance disclosed in the following patent documents: US 2008/214979, EP 1 762 263 and U.S. Pat. No. 7,104,763.

An example of MEMS micropump is disclosed in patent application WO 2010/046728. This MEMS micropump 1 as illustrated in FIG. 1 is a highly miniaturized and reciprocating membrane pumping mechanism. It is made from silicon or silicon and glass. It contains an inlet control member, here an inlet valve 2, a pumping membrane 3, a functional inner detector 4 which allows detection of various failures in the system and an outlet valve 5. The principle of such micro-pumps is known in the prior art, for example from U.S. Pat. No. 5,759,014.

Figure 1A:
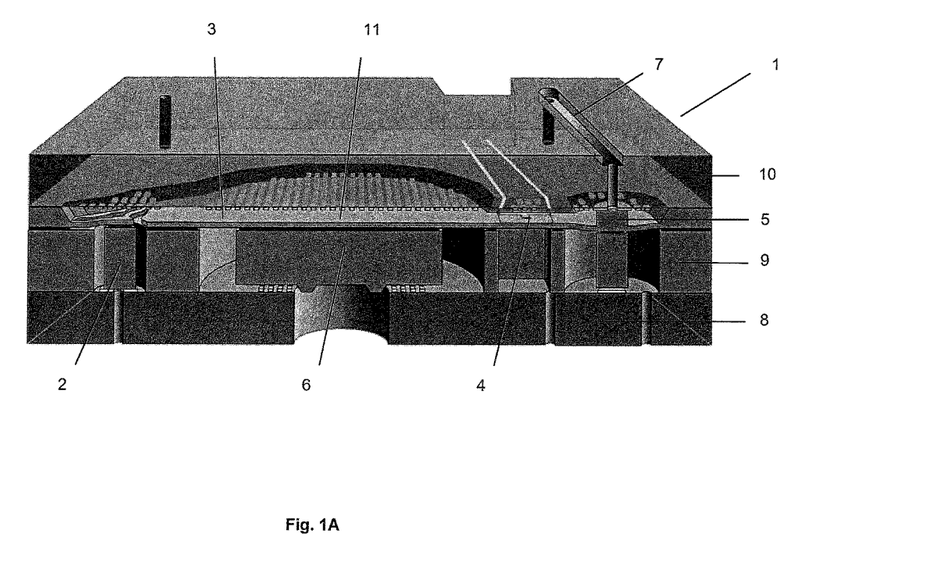

FIG. 1a illustrates a cross section of a micropump with the stack of a glass layer as base plate 8, a silicon layer as second plate 9, secured to the base plate 8, and a second glass layer 10 as a top plate, secured to the silicon plate 9, thereby defining a pumping chamber 11 having a volume.

An actuator (not represented here) linked to the mesa 6 allows the controlled displacement of the pumping membrane 3. A channel 7 is also present in order to connect the outlet control member, the outlet valve 5 to the outer detector not represented here and finally to the outlet port placed on the opposite side of the pump.

Figure 1B:
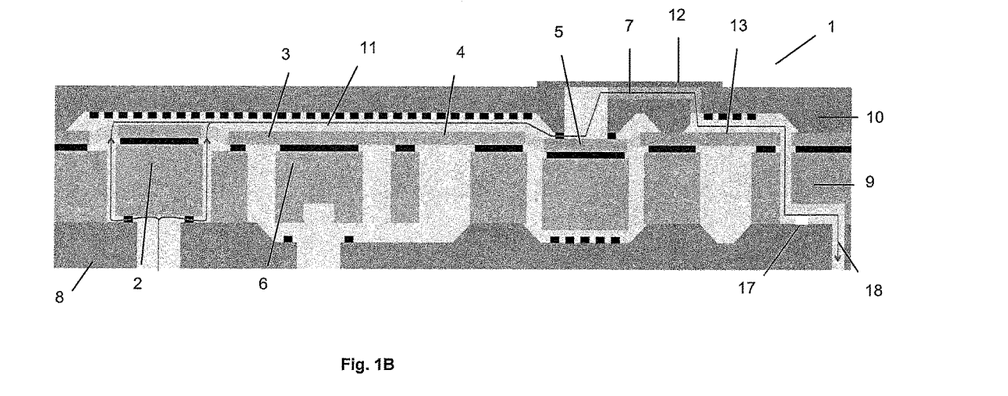

The FIG. 1b illustrates another cross-section of the MEMS micropump including a cover 12 onto the channel 7, the outer detector 13, the fluidic channel 17 between the outer detector 13 and the outlet port 18.

In the pump 1, the pressure inside the pumping chamber varies during a pumping cycle depending on numerous factors, such as the actuation rate, the pressure at the inlet and the outlet, the potential presence of a bubble volume, the valve characteristics and their leak rates.

Dysfunctions are detected by analysing the pressure profile during actuation cycles.

The inner pressure sensor 4 and outer pressure sensor 13 in the micro-pump 1 are made of a silicon membrane placed between the pumping chamber 11 and the pump outlet 5 and between the pump outlet valve 5 and pump outlet port 18 respectively. The sensors are located in a channel formed between the surface of the micro-pumps silicon layer 9 and its top layer 10. In addition, the sensors comprise a set of strain sensitive resistors in a Wheatstone bridge configuration on the membrane, making use of the huge piezo-resistive effect of the silicon. A change of pressure induces a distortion of the membrane and therefore the bridge is no longer in equilibrium. The sensors are designed to make the signal linear with the pressure within the typical pressure range of the pump. The fluid is in contact with the surface of the interconnection leads and the piezo-resistors. A good electrical insulation of the bridge is ensured by using an additional surface doping of polarity opposite to that of the leads and the piezo-resistors.

Because the analysis methods are performed during actuation (in-stroke detection), the occurrence of events like insulin reservoir pressurization or any other free flow conditions between two strokes are not detected. At low flow rate hazardous conditions may be therefore detected too late, leading to severe patient injuries.

There is therefore a need to improve the existing methods and systems for detection a malfunction of a MEMS micropump.

3. GENERAL DESCRIPTION OF THE INVENTION

The present invention offers several improvements with respect to state-of-the-art methods and systems.

The present invention, which may advantageously use the micropump described in WO 2010/046728 which is inside a device like described in the application EP11171155.2. The WO 2010/046728 describes out-of-stroke detection methods based on the analysis of at least one integrated pressure sensor. The EP11171155.2 describes medical device which comprises three distinct cavities where the pumping element is localised in the first cavity, the second cavity (which is the reservoir) is designed to contain a fluid for delivering to the patient. The first and second cavities are separated by a rigid wall while the second and third cavities are tightly separated by a movable membrane in such a manner said membrane may move between the second and third cavities when the volume of fluid changes. Said device comprises two distinct venting means, the first one for the first cavity and the second one for the third cavity. If one of venting means is clogged, the device may over or under delivery the fluid contained in the reservoir (the second cavity).

Using the method according to the present invention any condition that induces a free flow can be detected in few seconds. The amount of over or under delivery can be estimated. The method according to the invention also allows the detection of reservoir overfilling.

In a preferred embodiment the method according to the invention is based on the concept of equivalent fluidic resistance of both inlet and outlet valves.

Preferably, the residual fluidic resistances of the valves are determined during the last actuation cycle and the real time monitoring of the pressure inside the pumping chamber allows the determination of the maximum possible over or under delivery while out-of-stroke.

In-stroke and out-of-stroke detection methods are jointly used to alarm the patient as soon as possible of the occurrence of a risk of over or under delivery.

4. DETAILED DESCRIPTION OF THE INVENTION

The invention will be better understood with the following illustrated examples.

4.1. Pump Leakage

The pumping device is made of a reservoir comprising a particle and air filter, a MEMS micropump 1 having inlet (2) and outlet (5) check-valves, a pumping membrane (3) and integrated detectors (4 and 13) and means to connect the outlet (18) of the micropump to the patient body including e.g. a catheter.

All parts of the pumping device which are in contact with insulin define the fluidic pathway.

We define a leakage as any tightness defect that can lead to an over or under delivery We distinguish here two kinds of leakage
1. a leak from the fluidic pathway to outside, due to typically to:
   reservoir failure
   pumpchip crack
   septum issues
   needle issues
2. a leak within the fluidic pathway, due to typically to:
   particles below the valve seats
   cracks in the valve seats Leaks towards outside will usually induce under delivery. These kinds of leakage can be addressed by a test of the fluidic pathway tightness during production.

Crackguard rings are also implanted into the pumping membrane, the inlet and outlet valves. Any crack in the silicon opens electrically the crack-guard ring. The mechanical integrity of the movable or sensitive part of the micropump are therefore tested electrically during the functional test but also during the functioning of the device.

Leakage within the fluidic pathway can induce both over and under delivery.

The tightness of the valves prevents the direct communication between the insulin reservoir and the patient because even during actuation there is at least one valve normally close in the fluidic pathway.

The presence of particles below one valve seat induces a back-flow that affects the pump accuracy.

The presence of particles below both valves associated with a gradient of pressure between the inlet and the outlet induces a free flow.

Because there is a flow that can potentially transport particles below the valve seats, the test of valve tightness should be performed continuously while the test of tightness in production is sufficient to detect cracks of the valve seats because this is due to process issues only.

The present invention describes both in-production and in-functioning leak detection methods.

4.2. Valve Tightness and Equivalent Fluidic Resistance

We consider here a fully working pump unit, i.e. having passed all production tests with success. The fluidic pathway is therefore tight as well as the valves.

It is now important to discuss the notion of tightness because we are talking about flow rate of only few nanoliters per hour through hard valve seat having a finite roughness and no compliance.

We characterize a valve normally closed by its finite residual fluidic resistance $R_{in}$, and $R_{out}$, for the inlet and the outlet respectively.

Because the two fluidic resistances are placed in series, there is potentially a risk a free flow when the sum of their fluidic resistances $R_{in}+R_{out}$ reaches a threshold value and this independently of the individual values of $R_{in}$, and $R_{out}$.

After the dry functional test, we characterize the pressure decay from the pressurized pumping chamber through the normally close valves placed here in parallel. We can have therefore access to $R_{eq}$ only which is defined by:

$$R_{eq} = \frac{R_{in} R_{out}}{R_{in} + R_{out}}$$

This expression can be written in a more compact way:

$$1/R_{eq} = 1/R_{10} + 1/R_{out}$$

$R_{eq}$ is driven by the lowest value between $R_{in}$, and $R_{out}$. We define $R_{eq\ min}$ as the minimum allowed value during the functional test. This value is correlated to the max leak rate $Q_{max}$ allowed by the design input and by the minimum difference of pressure between the inlet and the outlet $\Delta P_{th}$ that can be detected by the pressure sensor.

The maximum leak rate is defined by:

$$Q_{max} = \frac{\Delta P_{th}}{R_{in} + R_{out}}$$

For a given value of $R_{eq}$ and $\Delta P_{th}$, the minimum value of the sum $R_{tot}=R_{in}+R_{out}$ is obtained for $R_{in}=R_{out}=2 R_{eq}$ as demonstrated below:

$$R_{tot} = R_{in} + R_{out} = \frac{R_{in} R_{out}}{R_{eq}}$$

Then $$R_{tot} = \frac{R_{out}^2}{R_{out} - R_{eq}}$$

The function $R_{tot}$ is minimal for a value of $R_{out}$ that nullifies the derivative:

$$\frac{\partial R_{tot}}{\partial R_{out}} = 0$$

We get $$2R_{out}(R_{out}-R_{eq})-R_{out}^2=0$$

And finally $R_{at}$ is minimized for $$R_{out}=R_{in}=2R_{eq}$$

In the worst case, the max leak rate $Q_{max}$ between the inlet and the outlet of the pump unit, for the pressure gradient $\Delta P_{th}$, is finally:

$$Q_{max} = \frac{\Delta P_{th}}{4R_{eq}}$$

To summarize, we define a pump unit as tight a pump unit having passed with success the dry test using the min value of $R_{eq\ min}$ for the equivalent fluidic resistances of the leak. This pump unit will exhibit in the worst case a max leak of $Q_{max}$ under the pressure gradient $\Delta P_{th}$ which corresponds to the minimum difference of pressure that can be detected by the integrated sensor.

4.3. Valve Tightness and Patient Safety

We simply review here the basic concepts around the valve tightness as an introduction to the detection methods.

To generate a leak (defined here as a flow from the reservoir to the patient) two elements are necessary:
 a leaky fluidic pathway
 a gradient of pressure.

Origin of the Finite Fluidic Resistance of the Valve

When the pump is not actuated, the system can be considered as a pressurized reservoir at the pressure $P_{in}$, which is connected to the patient at the pressure $P_{out}$ through two check valves having a finite residual fluidic resistance, a dead volume and a small elasticity in between.

Because the valve seats are not compliant to rigid particles, the risk of permanent opening shall be considered. The use of filter therefore limits the occurrence of a particle contamination but we cannot exclude particle release from the filter of the device itself or simply the displacement of a particle, which would be already present in the pump, below the valve seat during actuation. Leaks due to defect of the valve seats or defect of the bonding are detected during the functional test and are not considered here.

Pressure Gradient

In normal conditions $P_{in}$ is null or slightly negative by design: the reservoir is made of a thermoformed plastic soft pouch is soldered onto a hard shell; a small negative pressure is therefore needed to buckle the soft pouch towards the hard shell because of its dedicated shape. The range is typically 0/−10 mbar.

The pressure of the patient can be considered as null or slightly negative (−0.9+/−1.7 mbar according to E. Stranden and H. O. Myhre, Microvascular Research 24, 241-248 (1982), and −2.6 mbar according to Guyton and Hall, Textbook of Medical Physiology, Saunders Elsevier, twelfth edition (2011).

The additional pressure due to the water column height shall be considered. For patch device the maximum head height is few cm, inducing only few mbar between the reservoir and the patient.

In normal conditions the pump unit is safe because over infusion is prevented by the small and negative gradient of pressure between the reservoir and the patient.

We consider now deviations from the normal conditions: we can have overpressure in the reservoir due to an overfilling or due to a compression of the pumping unit external shell that should pressurize the reservoir. The pump unit should be able to detect any reservoir pressure conditions that make potential leakage hazardous for the patient even if no leakage is observed because this is an abnormal situation. The reservoir hard shell design is made to prevent the transmission of pressure to the reservoir soft pouch. The pump unit triggers an alarm when the pressure sensor in the pump "sees" a reservoir pressure larger than $\Delta P_{th}$ mbar. This pressure should be monitored in real time to alarm as soon as possible the patient of abnormal conditions.

Leak Detection, Back Flow and Free Flow

Valve leakage could induce:
 I. A back flow
 II. A free flow

A back flow is a leak induced under infusion during actuation in normal conditions. A leak at the inlet (outlet) induces a backflow during expulsion (suction) phase. These backflows corresponds in all cases to an under infusion. An alarm should be ideally triggered when the criterion on the pumping accuracy is not met. It is important to note that for the delivery accuracy it is no longer important to know if the inlet or the outlet or both are leaking. A criterion based on the equivalent fluidic resistance of the leak is enough to evaluate the infusion error due to leakage.

A free flow is a flow in delivery pathway which is not controlled by the pumping unit. A free flow is therefore an under or over infusion from the reservoir to the patient due to valve leakages out of specifications. Because the valves are placed in series both valves should exhibit a significant leak. As discussed previously abnormal pressure conditions should be also present to induce the flow.

To get a valve opening of 0.5 um for instance, it is necessary to have several spherical hard particles of 0.5 um onto the valve seat. The presence of only one particle induces a tilt of the valve that reduces significantly the fluidic resistance as illustrated below. Only one particle of 0.8 um onto the valve seat is equivalent to a valve aperture of 0.5 um.

The valves have also the capability to compress soft particles. In the present invention the worst case would be considered for analytical calculations: a particle of x um generates an opening of x um. Soft or non-spherical particles are not considered.

4.4. In-Stroke Leak Detection Principle

The in-stroke leak detection principle is based on the analysis of the pressure decay within the pumping chamber after actuation. The sensitivity of the method is due to the very low elasticity of the pumping chamber coupled to its very low dead volume.

Figure 2:
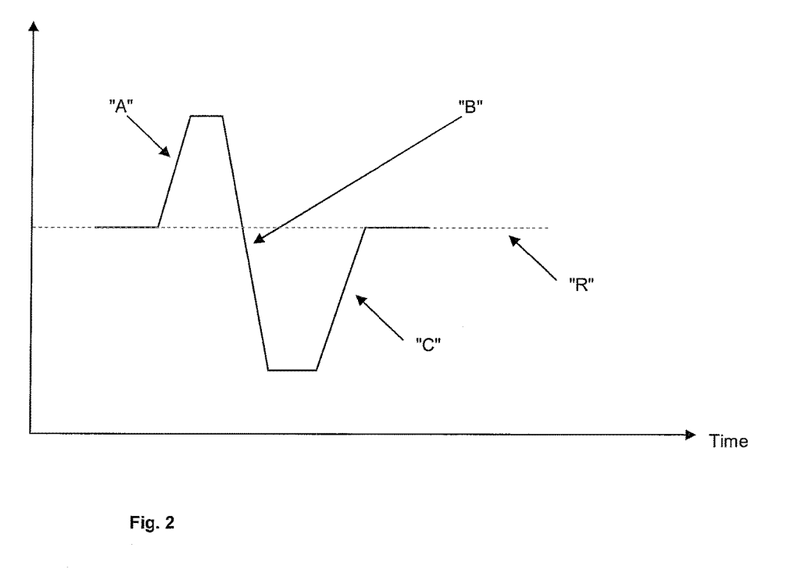

A typical pumping cycle has 3 phases according to FIG. 2:
 1) "A" is a ½ push of the pumping membrane starting for the rest position located between the two stop limiter towards the upper limiter (infusion)
 2) "B" is a full pull of the pumping membrane from the upper to the lower stop limiter (filling)
 3) "C" is a ½ push of the pumping membrane from the lower limiter to the rest position ("R") (infusion)

After the first or the third ½ push phases, the pressure in the pumping chamber is positive and equal to the outlet valve pretension for tight valves ($+P_{val\ out}$).

After the second pumping phase (filling), the pressure in the pumping chamber is negative and equal to the inlet valve pretension for tight valves ($-P_{val\ in}$).

The residual valve leakages induce a pressure decay that can be analyzed to determine their equivalent fluidic resistances $R_{eq}$. For very large leakage the backflow is too large to generate any pressure in the pumping chamber and the pressure remains constant.

When the pumping membrane is against a stop limiter (after the cycles 1 and 2), the elasticity of the pumping chamber is only limited to the detector membrane elasticity and the secondary deformation of the pumping and outlet membrane due to the pressure.

When the pumping membrane is located at its rest position without any voltage on the piezo actuator, the pumping chamber shows a much larger elasticity due to the pumping membrane at its rest position even by considering the stiffening induced by the short-circuited actuator tightly linked to it.

In all cases the presence of bubbles should be considered for the estimation of the elasticity.

The pressure decay after the phases 1 and 2 are therefore expected to be very fast while after the phase 3 we expect a slow decay.

We will focus on the analysis of the pressure decay after the phase 1 or 2.

4.5. Analytical Model

We distinguish two different methods for the leak detection: the dry test method, based on the analysis of the air pressure decay during a functional test, and the wet method used during the functioning of the pump. In both cases we should estimate the elasticity of the system. For the dry test we should focus on the air compressibility and the method is described firstly. For the wet test, because of the very low compressibility of the water, the elasticity of the pump is relevant. We provide therefore an estimation of the pumping chamber elasticity including potential bubbles and describe finally the in-functioning leak detection model.

Figure 3:
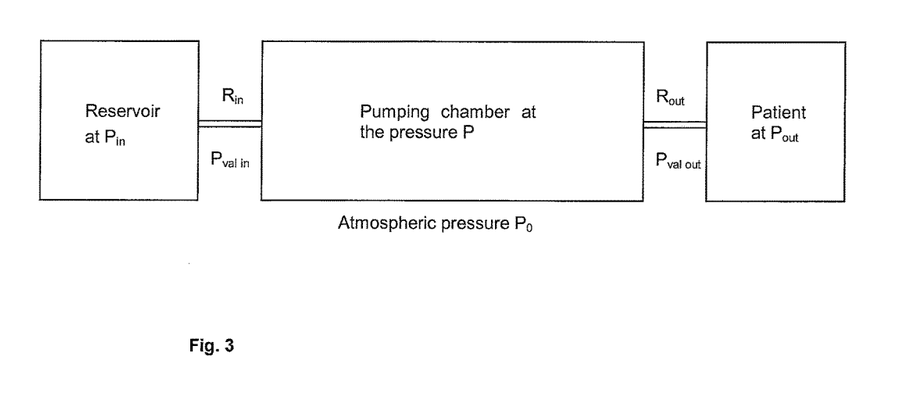

FIG. 3 shows a schematic fluidic model for the pumping device.

Leak Detection During Dry Test

The method is based on the pressure decay analysis in the pumping chamber after a compression and a blocking of the outlet valve which is obtained by applying a large pressure onto its vent.

We consider therefore an isothermal compression which reduces the pumping chamber volume from $V_S + V_D$ to $V_D$, where V is the stroke volume and $V_D$ is the dead volume.

We note n(t) the number of mole of gas and V the volume of the pump at the time t.

The total differential of the pressure is:

$$dP = \left(\frac{\partial P}{\partial n}\right)_V dn + \left(\frac{\partial P}{\partial V}\right)_n dV$$

We obtain, using the ideal gas law:

$$\frac{dP}{P} = \frac{dn}{n} - \frac{dV}{V}$$

In this expression, dn is the variation of the number of gas moles due to the isothermal flow and dV is the variation of volume due to the elasticity of the pump.

The variation of volume of the pump with the pressure is mainly due to the deformation of the different membranes (detector, actuation, outlet valve). We assume that this variation is linear:

$V = V_0 + \alpha_g(P - P_0)$

A variation of dP induces a variation of volume:

$dV = \alpha_g dP$

The quantity dn is related to the net flow Q during dt:

$$\frac{dn}{n} = \frac{Q}{V} dt$$

We obtain:

$$\frac{dP}{dt} = \frac{PQ}{V + \alpha_g P} = \frac{Q_{in} + Q_{out}}{\alpha_g + \frac{V}{P}}$$

The flows $Q_{in}$ and $Q_{out}$ are respectively the inflow and outflow in the pump.

For the dry test, we assume that the elasticity of the pump can be neglected when the pump is in contact with a stop limiter. The volume V is therefore constant and equal to $V_D$.

The former equation writes:

$$dt = -R_{eq} V_D \frac{dP}{P(P - P_0)} = \frac{R_{eq} V_D}{P_0} \left(\frac{1}{P} - \frac{1}{P - P_0}\right) dP$$

This equation can be easily solved and we obtain:

$$P = \frac{P_0}{1 - \left(1 - \frac{P_0}{P_{max}}\right) \text{Exp}\left[-\frac{P_0(t - t_0)}{R_{eq} V_D}\right]}$$

Where $P_{max}$ is the max pressure obtained at the end of the compression of the pumping chamber.

We note $\tau_{1/2}$ the time necessary to reduce the relative pressure by a factor 2:

$$\tau_{1/2} = \frac{R_{eq} V_D}{P_0} \ln\left[1 + \frac{P_0}{P_{max}}\right]$$

Typical values:

$R_{eq\ min}$=4E16 Pa·s/m$^{-3}$.

For nitrogen the value of $R_{eq\ min}$ is divided by 57 according to its viscosity.

If the criterion is verified, the max flow rate for water at 37° C., in the worst case, would be 0.032 ul/h for a pressure gradient of 100 mbar.

Elasticity of the System

Considering wet leak test, the elasticity of the pump a shall be included into the model.

The volume V(P) of the pump takes the form:

$V(P) = V_0 + \alpha(P - P_0) = V_{liquid} + V_{bubble}(P)$

Where $V_0$ is the volume of the pump at $P = P_0$.

Because of the very low compressibility of water we neglect the volume change of the liquid with the pressure.

The elasticity of the different parts of the pump is estimated here including the bubbles.

Pumping Membrane

If the membrane is in contact against a stop limiter, the membrane only undergoes a secondary distortion by applying pressure.

Typical values $\Delta V_{membrane}$=0.135 nl/100 mbar $\alpha_{membrane}$=1.35E-17 m$^3$/Pa If the pumping membrane is at its rest position, the elasticity is now driven by the membrane and the piezo bender.

The elasticity of the pumping membrane in that configuration is typically:

$\Delta V_{membrane}$=8.28 nl/100 mbar $\alpha_{membrane}$=8.28E-16 m$^3$/Pa

Detector
Typical values $$\Delta V_{detector}=0.25 \text{ nl}/100 \text{ mbar}$$

$$\alpha_{detector}=2.5\text{E-}17 \text{ m}^3/\text{Pa}$$

Outlet
The outlet valve is a circular membrane which shows the following typical elasticity if closed:

$$\Delta V_{outlet}=0.096 \text{ nl}/100 \text{ mbar}$$

$$\alpha_{outlet}=9.6\text{E-}18 \text{ m}^3/\text{Pa}$$

Figure 4:
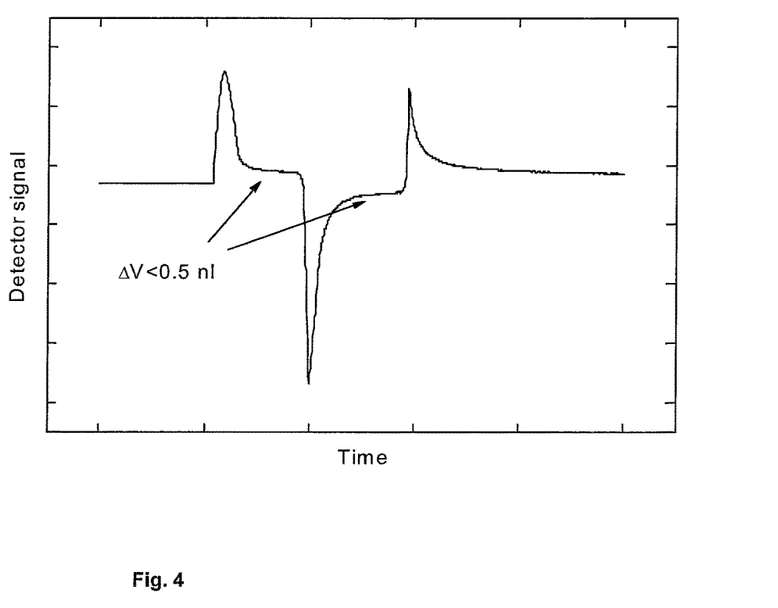

Pump Elasticity
When the pumping membrane is in contact with the stop limiters, when the valves are closed and when there is no bubble, the overall pump elasticity is the sum of the elasticity of the pumping membrane, the detector and the outlet membrane as shown in FIG. 4:

$$\Delta V_{pump}=0.48 \text{ nl}/100 \text{ mbar}$$

$$\alpha=4.8\text{E-}17 \text{ m}^3/\text{Pa}$$

When the piezo is not powered, the elasticity of the pump is mainly governed by the elasticity of the pumping membrane:

$$\Delta V_{pump}=8.625 \text{ nl}/100 \text{ mbar}$$

$$\alpha=8.625\text{E-}16 \text{ m}^3/\text{Pa}$$

Bubbles
According to the ideal gas law, we have:

$$V_{bubble}(P) = V_b(P) = \frac{P_0}{P} V_{b0}$$

Where P is the absolute pressure and $V_{bo}$ the volume of the bubble at $P=P_0$.

We note $P=P_0+P'$ where P' is the relative pressure.
If $P' \ll P_0$ we can do the following approximation that simplifies the model:

$$\frac{P_0}{P} = \frac{1}{1 + \frac{P'}{P_0}} \approx 1 - \frac{P'}{P_0} \approx 1 - \frac{P - P_0}{P_0}$$

We obtain:

$$V_b(P) \approx V_{b0}\left(1 - \frac{P - P_0}{P_0}\right) = V_{b0} + \alpha'(P - P_0)$$

With $$\alpha' = -\frac{V_{b0}}{P_0}$$

4.6. In-Functioning Leak Detection/Wet Leak Detection
For the test of pressure decay, the system can be seen as a pumping chamber at a pressure P with two fluidic resistances in parallel connected respectively to a pressure reservoir at $P_{in}$ and $P_{out}$ according to FIG. 3.

Volume of Liquid $V_{liq}$ in the Pumping Chamber
We consider all contributions to the system elasticity in the case of a pumping membrane being in contact with a stop limiter and the two valves being closed.

We have therefore:

$$V_{liquid}=V_0+\alpha(P-P_0)-V_b=V_0+\alpha(P-P_0)-V_{b0}-\alpha'(P-P_0)$$

Expression of the Pressure Decay
In order to estimate the evolution of the pressure just after the end of a stroke, i.e. when the relative pressure in the pumping chamber is equal to the inlet pretension (after a fill) or the outlet pretension (after an infusion), we simply write the equation of the matter conservation:

$$Q + \frac{dV_{liquid}}{dt} = 0$$

We can write, since the flow is laminar:

$$Q = -\frac{dV_{liquid}}{dt}$$
$$= \frac{P - P_0 - P'_{in}}{R_{in}} + \frac{P - P_0 - P'_{out}}{R_{out}}$$
$$= -(\alpha - \alpha')\frac{dP}{dt}$$
$$= \frac{P - P_0}{R_{eq}} - \frac{P'_{in}}{R_{in}} - \frac{P'_{out}}{R_{out}}$$

Where $P_{in}'$ and $P_{out}'$ are relative pressures $$\begin{cases} P_{in} = P_0 + P'_{in} \\ P_{out} = P_0 + P'_{out} \end{cases}$$

We note $$\varepsilon = \frac{R_{in}}{R_{out}}$$

$$\chi = \frac{P'_{in}}{R_{in}} + \frac{R'_{out}}{R_{out}}$$

$$\xi = \chi R_{eq} = \frac{P'_{in}}{1+\varepsilon} + \frac{P'_{out}}{1+\frac{1}{\varepsilon}}$$

$$\lambda = \frac{1}{R_{eq}(\alpha - \alpha')}$$

And $$\beta = P'_{out} + P_{val\ out} - \chi R_{eq} = P'_{out} + P_{val\ out} - \xi$$

Thus $$\chi R_{eq} = \frac{P'_{in}}{1+\varepsilon} + \frac{P'_{out}}{1+\frac{1}{\varepsilon}}$$

We obtain:

$$\frac{dP}{P - P_0 - \chi R_{eq}} = -\frac{dt}{R_{eq}(\alpha - \alpha')} = -\lambda dt$$

Thus $$\ln(P - P_0 - \chi R_{eq}) = -\frac{t - t_0}{R_{eq}(\alpha - \alpha')} + v$$

Where $\upsilon$ is an integration constant.

During the infusion, just after the push move of the membrane (i.e. when the outlet valve closes) the pressure in the pumping chamber is equal to:

$$P(t_0) - P_0 = P'_{out} + P_{val\ out} = \chi R + e^{\upsilon}$$

Finally the expression of the relative pressure $P-P_0$ in the pumping chamber takes the form:

$$P - P_0 = \chi R_{eq} + (P'_{out} + P_{val\ out} - \chi R_{eq})e^{-\frac{t-t_0}{R_{eq}(\alpha-\alpha')}}$$
$$= \xi + \beta e^{-\lambda(t-t_0)}$$

Or $$P - P_0 = \frac{P'_{in}}{1+\varepsilon} + \frac{P'_{out}}{1+\frac{1}{\varepsilon}} + \left(P'_{out} + P_{val\ out} - \frac{P'_{in}}{1+\varepsilon} - \frac{P'_{out}}{1+\frac{1}{\varepsilon}}\right)e^{-\frac{(t-t_0)(1+\varepsilon)}{R_{in}(\alpha-\alpha')}}$$

During the time $\tau$ after $t_0$, the total volume of liquid $\Delta V_{liq}$ that flows outside the pumping chamber is:

$$\Delta V_{liq} = \int_{t_0}^{t_0+\tau} \frac{P - P_0 - P'_{in}}{R_{in}} dt + \int_{t_0}^{t_0+\tau} \frac{P - P_0 - P'_{out}}{R_{out}} dt$$
$$= \int_\tau dt' \left[\frac{\xi - P'_{in} + \beta e^{-\lambda t}}{R_{in}} + \frac{\xi - P'_{out} + \beta e^{-\lambda t}}{R_{out}}\right]$$

Finally we obtain $$V_{tot} = \frac{\beta}{\lambda}\left(\frac{1 - e^{-\lambda \tau}}{R_{eq}}\right)$$

Pressure Leak Threshold

We set the leak alarm threshold at the relative pressure $P_{leak}$ and we can estimate, according to the environment conditions and the device characteristics, the duration $\tau_{leak}$ necessary to reduce the pumping chamber pressure from the relative pressure $P_{val\ out}$ towards $P_{leak}$ is:

$$\tau_{leak} = -\frac{1}{\lambda} \ln\left[\frac{P_{leak} - \xi}{\beta}\right]$$

It is therefore possible to simulate the duration $\tau_{leak}$ by varying all parameters of the previous formula according to their respective ranges.

In the following detailed form, it is possible to see all terms that affect $\tau_{leak}$:

$$\tau_{leak} = -R_{eq}(\alpha - \alpha')\ln\left[\frac{P_{leak} - R_{eq}\left(\frac{P'_{in}}{R_{in}} + \frac{P'_{out}}{R_{out}}\right)}{P'_{out} + P_{val\ out} - R_{eq}\left(\frac{P'_{in}}{R_{in}} + \frac{P'_{out}}{R_{out}}\right)}\right]$$

Considering the in-functioning criterion for the leak rate, we compare the measured duration $\tau_{leak\ mes}$ a specification $\tau_{spec}$: the device is acceptable in term of leak rate if $$\tau_{leak\ mes} \geq \tau_{spec}$$

Leak Criterion Based on the Worst Case Conditions of Free Flow: In-Stroke Detection The in-functioning leak test gives an indication of the equivalent fluidic resistance of the valve leaks $R_{eq}$.

We measure $\tau_{leak\ mes}$ and we would like to know in the worst case what is the biggest leak rate associated to that measurement.

1. We determine first the conditions necessary to obtain the lowest $R_{eq}$ corresponding to $\tau_{leak\ mes}$ and we derive $R_{eq}$
2. We determine the worst configuration for $R_{in}$ and $R_{out}$ according to $R_{eq}$
3. We determine the max leak rate $Q_{max}$ from the reservoir towards the patient in the worst case For a given $R_{eq}$, the max leak from the reservoir to the patient is met for:

$$R_{out} = R_{in} = 2R_{eq}$$

$$R_{eq} = -\frac{\tau_{leak\ mes}}{(\alpha - \alpha')\ln\left[\frac{P_{leak} - \frac{P'_{in}}{2} - \frac{P'_{out}}{2}}{P_{val\ out} + \frac{P'_{out}}{2} - \frac{P'_{in}}{2}}\right]}$$

The measurement of $R_{eq}$ depends on the pressure conditions at the inlet and the outlet as well as the quantity of air inside the pumping chamber. The detector launches an alarm when the pressure in the reservoir exceeds $P_{in\ th}$ and when the bubble in the pump exceed $V_{b\ th}$ (with the corresponding value of $a'_{th}$). We assume that the pressure at the outlet is null.

Thus $$R_{eq} = -\frac{\tau_{leak\ mes}}{(\alpha - \alpha'_{th})\ln\left[\frac{P_{leak} - \frac{P'_{in\ th}}{2}}{P_{val\ out} - \frac{P'_{in\ th}}{2}}\right]}$$

As discussed before, in the worst case, the max leak rate from the reservoir to the patient that can be obtained for a given $R_{eq}$ is:

$$Q_{max} = \frac{\Delta P_{th}}{4R_{eq}} = -\frac{P'_{in\ th}}{4\tau_{leak\ mes}}(\alpha - \alpha'_{th})\ln\left[\frac{P_{leak} - \frac{P'_{in\ th}}{2}}{P_{val\ out} - \frac{P'_{in\ th}}{2}}\right]$$

Where $\Delta P_{th}$ is the max gradient of pressure between the inlet and the outlet that can be present without launching an alarm.

We have therefore associated a maximum leak rate, according to the worst external conditions to the measured value of $\tau_{leak\ mes}$.

It is now possible to associate the specification in term of leak rate of the design input with a value of $\tau_{leak\ max\ DI}$:

$$Q_{max\ DI} = -\frac{P'_{in\ th}}{4\tau_{leak\ max\ DI}}(\alpha - \alpha'_{th})\ln\left[\frac{P_{leak} - \frac{P'_{in\ th}}{2}}{P_{val\ out} - \frac{P'_{in\ th}}{2}}\right]$$

In that configuration, if $\tau_{leak\ mes} \geq \tau_{leak\ max\ DI}$ we can ensure at 100% that the device is safe. If this criterion is too conservative, Monte Carlo simulations are desirable to determine a good trade-off between safety and false alarm rating.

To illustrate this point we propose the following numerical application:

$P_{leak}$=50 mbar
$P_{in\ th}'$=50 mbar
$P_{val\ out}$=110 mbar
$\alpha$=4.8E-17 m$^3$/Pa
bubble size threshold=10 nl
$\Rightarrow \alpha'$=-1E-16 m$^3$/Pa
$Q_{max\ DI}$=0.179 U/h
$\Rightarrow \tau_{leak\ max\ DI}$=0.455 s The time necessary to reduce the relative pressure by a factor 2 (i.e. from 100 to 50 mbar) is therefore 0.455 s according to these worst conditions.

Without bubbles, this time constant is only 0.148 s.

In normal conditions of pressure, the max gradient of pressure is 18.6 mbar.

We obtain:

$\tau_{leak\ max\ DI}$=0.1254 s with bubble of 10 nl
$\tau_{leak\ max\ DI}$=0.041 s without bubble The analytical model can be used to determine a $\tau_{spec}$ value that is acceptable in term of risk for the patient and that will launch too much false alarm: a high value of $\tau_{spec}$ is conservative in term of patient safety but the too high number of false alarm is not acceptable in term of usability.

The opposite situation with a small $\tau_{spec}$ is no longer acceptable because true alarms will be missed.

Leak Criterion Based on the Pumping Accuracy

Without any upstream or downstream pressure, a leak can induce a backflow that reduces the net pumped volume.

In bolus mode, we assume in a first approximation that the mean pressure during the positive or negative peak of pressure is +/-Pmax mbar during a maximum duration of T ms.

We assume a backflow at the inlet. The backflow can be determined by integrating the pressure profile and by dividing this by the fluidic resistance of the backflow $Rf_{backflow}$.

Typical values:

$Rf_{backflow}$=4E14 Pa·s/m$^3$.

This corresponds to a typical opening of about 1 to 1.5 um.

Since $R_{eq} \approx R_{backflow}$, we obtain:

$$\tau_{leak} = -R_{eq}(\alpha - \alpha')\ln\left[\frac{P_{leak}}{P_{val\ out}}\right]$$

Using
$P_{leak}$=50 mbar
$P_{val\ out}$=100 mbar
$\alpha$=4.8E-17 m$^3$/Pa
bubble size threshold=10 nl
$\Rightarrow \alpha'$=-1E-16 m$^3$/Pa
We obtain
$\Rightarrow \tau_{leak}$=0.041 s During the infusion, the pressure shows a peak of pressure and after about 100 ms the pressure should be more or less equal to the outlet valve pretension. If the pressure decay is fast enough to reduce this pressure by a factor 2 in less than 41 ms, then we expect in this worst case an error on the accuracy larger than 5%.

Without bubble, this time is divided by 3, leading to a quasi instantaneous pressure release to $P_0$ after the actuation (less than 13.6 ms).

We can conclude that the criterion on the delivery accuracy is much easier to be met than the criterion on the leakage.

This estimation shows that we should consider the leak criterion based on the free flow and not on the back flow.

Figure 5:
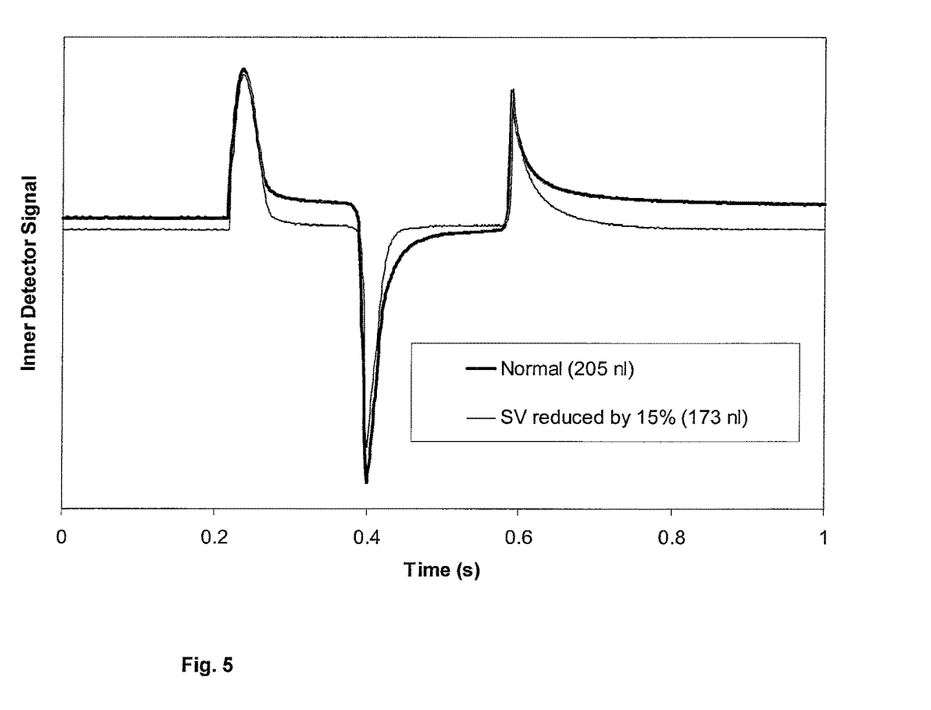

The FIG. 5 shows typical detector signals using the actuation profile given in FIG. 2 for a tight pump (bold line) and a pump having a back flow of 15% (thin line).

According to the examples provided above the fast pressure decay after actuation is very fast in presence of back flow.

4.7. Leak Detection and Static Pressure Measurement: Out-of-Stroke Detection

At slow basal rate, the pressure in the pumping chamber shall be monitored to check eventual reservoir over or under pressure.

To investigate the effect of a static pressure at the inlet, we assume that in case of constant inlet pressure, the valves are either together open or together closed.

We distinguish therefore two cases:
1. $P-P_{out} > P_{val\ out}$
2. $P-P_{out} < P_{val\ out}$ Case 1: Static Pumping Chamber Pressure>Outlet Valve Pretension In the case 1, because the outlet valve is open, the inlet valve is automatically open and the inlet pressure is therefore larger than $P_{val\ in} + P_{val\ out} + P_0$. In that configuration of large overpressure (larger than the sum of the valve pretensions) the flow is very large. We assume that the fluidic resistances of the valves are equivalent in that configuration. To estimate the max flow rate, we only consider the fluidic resistances of the valves and we do not consider singular head losses.

Figure 6:
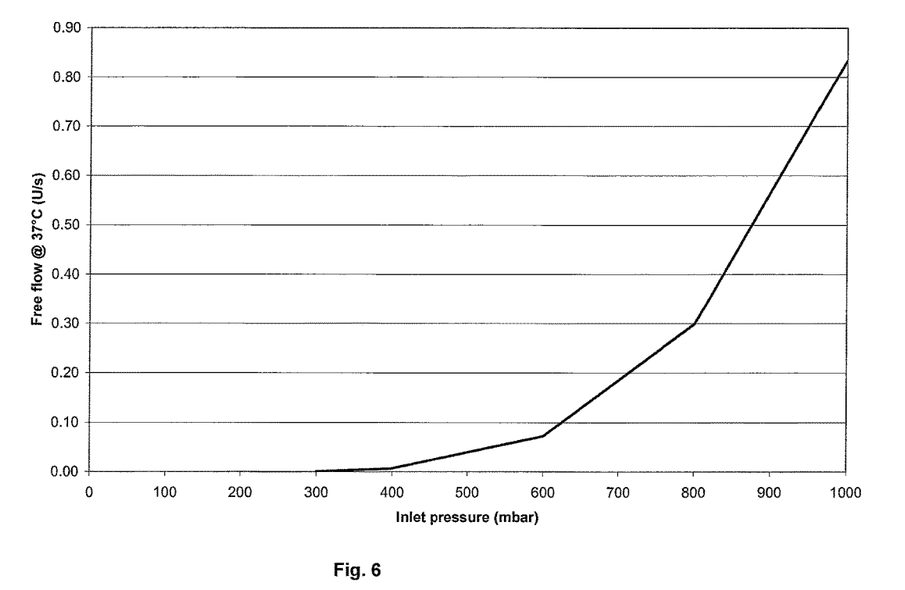

The FIG. 6 shows the typical maximum flow rate at 37° C. using the former approximation:

The pressure P in the pumping chamber is here the half of the inlet pressure.

Case 2: Static Pumping Chamber Pressure<Outlet Vale Pretension

The pump is in basal configuration. During the last stroke the equivalent fluidic resistance of the valves has been estimated and there is no alarm and no inlet overpressure.

We suppose the inlet pressure rises to a value $P_{in}$. The pressure in the pumping chamber is equal to P with P<100 mbar. In this configuration both valves are closed. We can assume that from the last stroke the residual leaks of the valves do not change. The equivalent fluidic resistance $R_{eq}$ of the valves is therefore known.

We try to estimate in the worst case what is the max free flow $Q_{max}$ for a measured value of P and a given value of $R_{eq}$.

We have already shown that for a given $P_{in}$ and a given $R_{eq}$, the max flow rate is obtained when $$P_{in} - P_0 = \frac{P - P_0}{2}$$

This rule is unfortunately not reciprocal.

The max inlet pressure is equal to $P+P_{val\ in}$ (otherwise the inlet valve is open in contradiction to the discussion hereabove).

We will now use the max leak rate theorem.

Max Leak Rate Theorem

If $P-P_0 < P_{val\ out}$, and for a given $R_{eq}$ of the valves, the max leak rate is obtained for $P_{in} = P + P_{val\ in}$ This theorem is demonstrated using a proof by contradiction.

Demonstration:

We consider a system having a pressure P in the pumping chamber, an equivalent fluidic resistance of the valves $R_{eq}$ and a pressure $P_{in} < P\ P_{val\ in}$ inducing a leak rate Q.

We will show that for any increase of inlet pressure $\delta P_{in}$ from any $P_{in}$ up to $P + P_{val\ in}$ there is always a couple of values $R_{in}$, and $R_{out}$ values that keeps constant $R_{eq}$ and P and that lead to a flow rate larger than Q.

We have:

$$\begin{cases} Q = \dfrac{P_{in} - P_0}{R_{in} + R_{out}} = \dfrac{P - P_0}{R_{out}} \\ \text{and} \\ Q' = \dfrac{P_{in} + \delta P_{in} - P_0}{R'_{in} + R'_{out}} = \dfrac{P - P_0}{R'_{out}} \end{cases}$$

We will show that there are values $R'_{in}$ and $R'_{out}$ that ensure that $Q' > Q$.

$$R_{eq} = \frac{R_{in} R_{out}}{R_{in} + R_{out}}$$
$$= \frac{R'_{in} R'_{out}}{R'_{in} + R'_{out}}$$
$$= \frac{R_{in}}{1 + \varepsilon}$$
$$= \frac{R'_{in}}{1 + \varepsilon'}$$
$$= \frac{R_{out}}{1 + \dfrac{1}{\varepsilon}}$$
$$= \frac{R'_{out}}{1 + \dfrac{1}{\varepsilon'}}$$

With $$\begin{cases} \varepsilon = \dfrac{R_{in}}{R_{out}} = \dfrac{P_{in} - P_0}{P - P_0} - 1 \\ \varepsilon' = \dfrac{R'_{in}}{R'_{out}} = \dfrac{P_{in} + \delta P_{in} - P_0}{P - P_0} - 1 \end{cases}$$

We obtain:

$$R'_{in} = \left(1 + \frac{\delta P_{in}}{P_{in} - P_0}\right) R_{in} > R_{in}$$

And $$R'_{out} = \frac{(P_{in} - P)}{(P_{in} + \delta P_{in} - P)} \times \frac{(P_{in} - P_0 + \delta P_{in})}{(P_{in} - P_0)} R_{out}$$
$$= \frac{1 + \left(\dfrac{\delta P_{in}}{P_{in} - P_0}\right)}{1 + \left(\dfrac{\delta P_{in}}{P_{in} - P}\right)} R_{out}$$

For $P > P_0$ we check that $R'_{out} < R_{out}$ as expected for $Q' > Q$.

We have therefore demonstrated that the max flow is obtained for $P_{in} = P + P_{val\ in}$.

The max leak rate takes the form:

$$Q_{max} = \frac{P + P_{val\ in} - P_0}{R_{in} + R_{out}} = \frac{P - P_0}{R_{out}}$$

The max flow rate is obtained for:

$$\varepsilon = \frac{R_{in}}{R_{out}} = \frac{P_{val\ in}}{P - P_0}$$

Finally, the max leak rate, for a given $R_{eq}$ and a given static pressure P in the pumping chamber, takes the form:

$$Q_{max} = \frac{P - P_0}{R_{eq}\left(1 + \dfrac{P - P_0}{P_{val\ in}}\right)} = \frac{1}{R_{eq}\left(\dfrac{1}{P - P_0} + \dfrac{1}{P_{val\ in}}\right)}$$

We can compare the accuracy of this out-of-stroke leak detection with the in-stroke detection as described hereabove.

We consider now an in-stroke detection threshold of 50 mbar leading to a max leak rate of 0.179 U/h: we obtain $R_{eq} = 2.514E15$ Pa·s/m$^3$.

Figure 7:
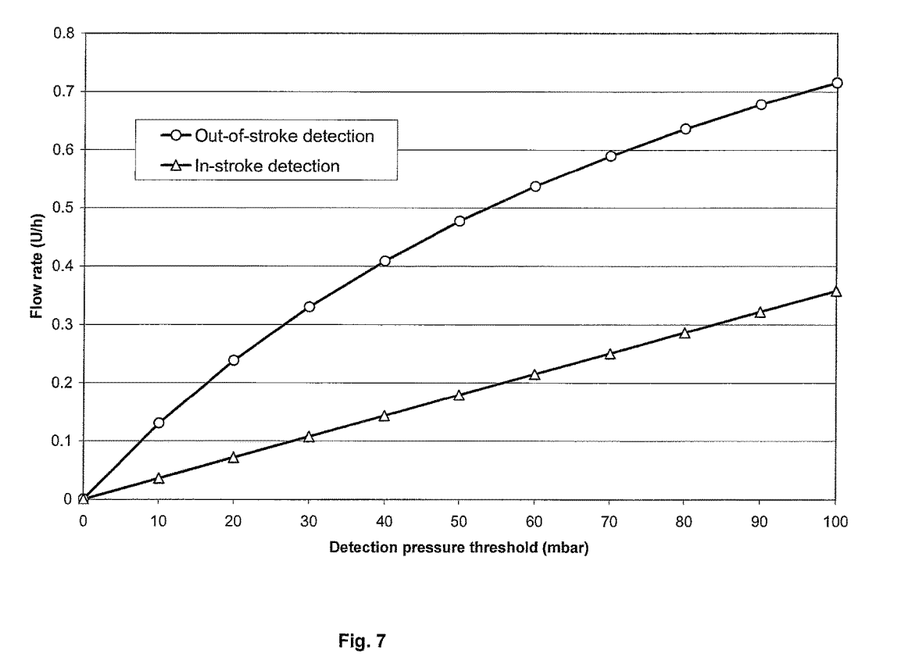

The FIG. 7 shows the max leak rate in U/h that can be detected using in-stroke and out-of-stroke detection as a function of the detection pressure threshold:

The measurement of the inner detector to check a possible inlet overpressure is mandatory. The main issue of this measurement is that the inner detector is not sensitive to inlet pressure lower than 100 mbar if the ratio $$\varepsilon = \frac{R_{in}}{R_{out}}$$

is large. This effect is due to the inlet valve pretension. During the stroke, the inlet valve opens and the detector directly "sees" the reservoir pressure.

Even if the out-of-stroke detection of the leak is two at four times less sensitive than during a stroke, this method gives fundamental improvement in term of patient safety because of the continuous estimation of the maximum leak rate in the worst case, without additional stroke and with limited power consumption.

To summarize, the monitoring of the inner (4) and outer (13) detector signals, when the pump is not actuated, is used to detect under or over pressure onto the reservoir and to estimate the related maximum over or under infusion.

4.8. Static Load on Reservoir Housing

Static load could be detected by the pressure sensors without actuating the pump if it results:

1. an increase of the reservoir pressure
2. or an increase of the interstitial pressure If the static load transmits a force directly onto the reservoir membrane, the reservoir pressure increases as well as the downstream pressure according to the discussion here above. A static measurement of the inner pressure sensor (4) is used to detect the effect of the static load.

If the static load transmits a force directly onto the patient skin around the cannula, typically for patch pump, the tissue compression will increase the interstitial pressure and therefore the pressure at the pump outlet (18) because the insulin will transmit this pressure. The two pressure sensors (4 and 13) and more especially the sensor (13) at the outlet of the pump will directly see this pressure increase.

4.9. Vent Clogging

The first and third cavities (described in the application EP11171155.2) have venting means to prevent any pressurization. If one of said venting means get clogged, the pressure gradient between inside device and external environment may change inducing an over or under delivery.

Figure 8:
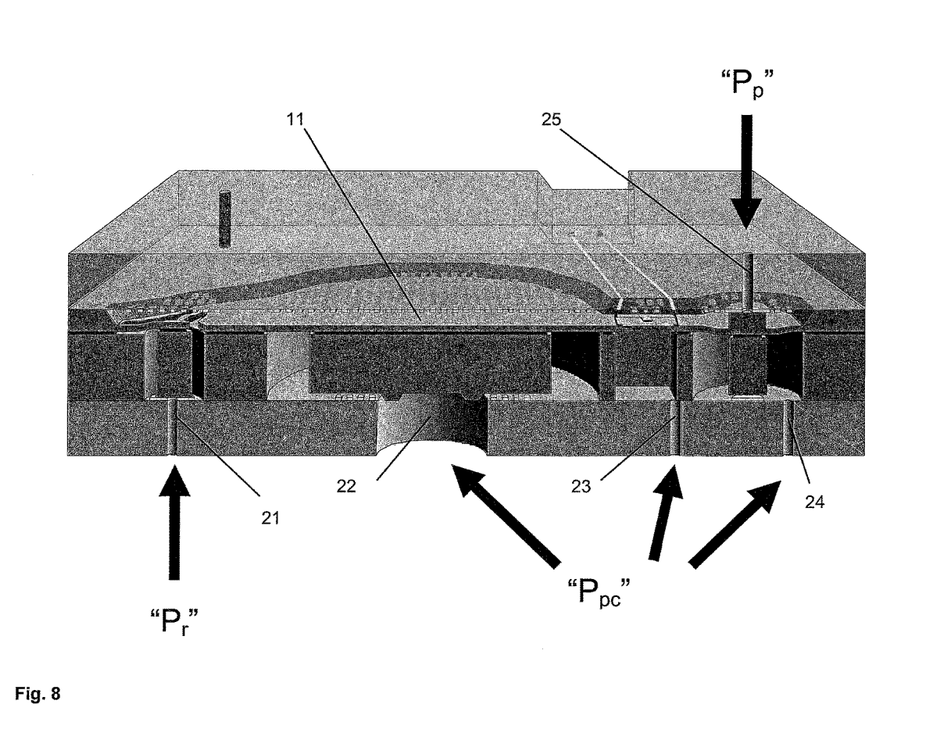

The FIG. 8 shows the pumping device and its different ports. The inlet valve port (21) is connected to the reservoir wherein a pressure form the reservoir ("$P_r$"). The outlet valve port (25) is connected to the patient wherein a pressure form the patient ("$P_r$"). The membrane port (22), the inner detector port (23) and the outer detector port not represented here are connected to the pump controller that includes the actuator wherein a pressure ("$P_{pc}$"). The outlet valve has a specific venting port 24 which is used during functional test as described in the document WO 2010/046728.

In another embodiment, the document WO2007113708 shows for instance a pumping device wherein the reservoir and the pump controller (actuator, driving electronics and batteries) share the same venting hole towards outside.

In case of vent clogging, a positive or negative pressure may be trapped in the reservoir housing and/or in the pump controller.

The change of pressure due to clogging can be monitored using the two sensors of the pump even without actuation.

Vent Clogging Case Studies:
1. clogging of reservoir vent
   ⇒ Detection using inner pressure sensor (see 4.6 to 4.8)
2. clogging of pump controller vent only
   ⇒ The sensor membrane back side (which is not in contact with the liquid) will be pressurized e.g. via the port (23) for the inner detector (4), inducing a deflection of the membrane and therefore a signal change. Positive (respectively negative) pressure on the port (23) is equivalent to a negative (resp. positive) pressure in the pumping chamber (30).
3. clogging of all venting ports
   ⇒ The same pressure is observed in the reservoir and in the pump controller, therefore the outer detector (13) membrane, which is connected on one side with the patient and on the other side with the pump controller, is able to detect any pressure changes in the pump controller.

The clogging of the outlet valve port (24) only will be detected during actuation if the cavity below the outlet valve is pressurized. This pressure will induce an offset on the outlet valve opening threshold and this offset can be detected according to the methods described in the document WO 2010/046728. This clogging is only possible during the mounting of the pump controller onto the reservoir.

4.10. Reservoir Filling Monitoring

The reservoir should be filled with a given quantity of liquid. In case of overfilling, the device should prime the pump and actuate in order to limit the pressure in the reservoir due to this overfilling.

The activation of the inner (4) and outer (13) detectors during the filling is therefore useful to alarm the patient of any reservoir overpressure using vibrations, visual or audible alarms.

Functional pumps are characterized in production. The equivalent fluidic resistance is determined with a criterion for the minimum value allowed. Since the pump has never been actuated between the production and the filling, the minimum equivalent fluidic resistance is known. The measurement of the pressure during the filling gives therefore an indication of the flow rate through the pump. For very large overpressure, the valves open and the flowrate becomes driven by the curve shown in FIG. 6.

The alarm is triggered when the pressure in the pumping chamber is larger than a predefined value. The alarm may be triggered continuously if the pressure remains larger than this predefined value and may be stopped only once the pressure is decreased below this predefined value. The pressure release may be performed by the patient himself who can either remove liquid by pulling on the syringe piston or simply by releasing the syringe piston.

At the end of the filling, the pressure in the reservoir may be large in case of overfilling. The pressure is therefore monitored while the pump is actuated continuously during the time necessary to reduce the pressure up to a predefined threshold value. The pump is then actuated a predefined number of cycles in order to ensure that the relative reservoir pressure is equal or very close to zero.

The invention claimed is:

1. A medical device comprising a pumping device having an inner pressure sensor arranged to measure a pressure in a pumping chamber, an external reservoir in fluid communication with the pumping chamber of the pumping device, a notification device and a processing unit, wherein the processing unit is configured to
   monitor a signal of the inner pressure sensor during a filling of the reservoir;
   trigger a notification with the notification device when a first threshold pressure signal is reached during the filling of the reservoir; and
   continuously actuate the pumping device to remove a determined volume of fluid from the reservoir, after the triggering of the notification.

2. The medical device according to claim 1, wherein during the filling the pumping device is in a rest position.

3. The medical device according to claim 1, wherein the processing unit is further configured to stop the notification when the signal of the inner pressure sensor is lower than a predefined threshold.

4. The medical device according to claim 1, wherein the processing unit is further configured to stop the pumping actuation when a predefined number of strokes have been reached.

5. The medical device according to claim 1, wherein the processing unit is further configured to stop the pumping actuation after a predetermined time period.

6. The medical device according to claim 1, wherein the processing unit is further configured to stop the pumping actuation when a predefined threshold for the signal of the inner pressure sensor has been reached.

7. The medical device according to claim 1, wherein the reservoir includes a predefined volume.

8. The medical device according to claim 1, wherein in continuously actuating the pumping device, the determined volume of fluid is removed from the reservoir such that a volume of fluid remaining in the reservoir reaches a predefined value.

9. The medical device according to claim 1, wherein the pumping device further comprises a pumping membrane, and the pressure sensor is arranged to be in operative connection with the pumping membrane of the pumping chamber.

10. The medical device according to claim 1, wherein the pumping device further comprises a pumping membrane and an actuator for actuating the pumping membrane, wherein during the filling, the pumping membrane is in a rest position.

11. The medical device according to claim 1, wherein the pumping device further comprises a pumping membrane and an actuator for actuating the pumping membrane, wherein during the filling, the actuator of the pumping membrane is not powered.

* * * * *